(12) United States Patent
Ho et al.

(10) Patent No.: US 9,242,273 B2
(45) Date of Patent: Jan. 26, 2016

(54) METHOD FOR OPERATING CMUTS UNDER HIGH AND VARYING PRESSURE

(71) Applicant: The Board of Trustees of the Leland Stanford Junior University, Palo Alto, CA (US)

(72) Inventors: Min-Chieh Ho, Palo Alto, CA (US); Mario Kupnik, Cottbus (DE); Butrus T. Khuri-Yakub, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/648,995

(22) Filed: Oct. 10, 2012

(65) Prior Publication Data
US 2013/0087867 A1    Apr. 11, 2013

Related U.S. Application Data

(60) Provisional application No. 61/545,788, filed on Oct. 11, 2011.

(51) Int. Cl.
*H01L 29/84* (2006.01)
*B06B 1/02* (2006.01)
*G01N 29/24* (2006.01)

(52) U.S. Cl.
CPC .......... *B06B 1/0292* (2013.01); *G01N 29/2406* (2013.01); *H01L 29/84* (2013.01)

(58) Field of Classification Search
USPC ............ 257/415–419, E29.324; 438/53, 455; 310/300, 309; 600/459; 381/191; 29/594
See application file for complete search history.

(56) References Cited

U.S. PATENT DOCUMENTS

| | | | |
|---|---|---|---|
| 7,047,814 B2 * | 5/2006 | Zias et al. ........................ | 73/718 |
| 7,274,623 B2 | 9/2007 | Bayram et al. | |
| 7,675,221 B2 | 3/2010 | Machida et al. | |
| 2005/0219953 A1 | 10/2005 | Bayram et al. | |
| 2009/0322181 A1 | 12/2009 | Machida et al. | |
| 2010/0207484 A1 * | 8/2010 | Chang ........................... | 310/300 |
| 2010/0207485 A1 | 8/2010 | Dirksen et al. | |
| 2011/0040189 A1 | 2/2011 | Petruzzello et al. | |
| 2011/0095645 A1 * | 4/2011 | Chang ........................... | 310/300 |
| 2012/0010538 A1 * | 1/2012 | Dirksen ........................... | 601/2 |
| 2012/0133005 A1 * | 5/2012 | Langeries et al. ............ | 257/416 |

FOREIGN PATENT DOCUMENTS

| | | | | |
|---|---|---|---|---|
| NL | 2269746 | * | 5/2011 | ............... B06B 1/02 |
| WO | WO 2009/041675 | * | 4/2009 | ............... B06B 1/02 |

* cited by examiner

*Primary Examiner* — Thao X Le
*Assistant Examiner* — Gardner W Swan
(74) *Attorney, Agent, or Firm* — Lumen Patent Firm

(57) ABSTRACT

Capacitive micromachined ultrasonic transducers (CMUTs) in permanent contact mode are provided. Such a CMUT always has its plate in contact with the substrate, even for zero applied electrical bias. This contact is provided by the pressure difference between the environment, and the pressure of the evacuated region between the CMUT plate and substrate. Due to this permanent contact, the electric field in the gap for a given DC bias voltage will be larger, which provides improved coupling efficiency at lower DC bias voltages. Furthermore, in an environment with high and varying pressure, the plate will not shift between the conventional mode and the collapsed mode, but will only be pushed down with varying contact radius. In some embodiments, an electrode shaped as an annulus is employed, so that only the active vibrating part of the CMUT plate sees the applied DC and AC voltages.

3 Claims, 12 Drawing Sheets

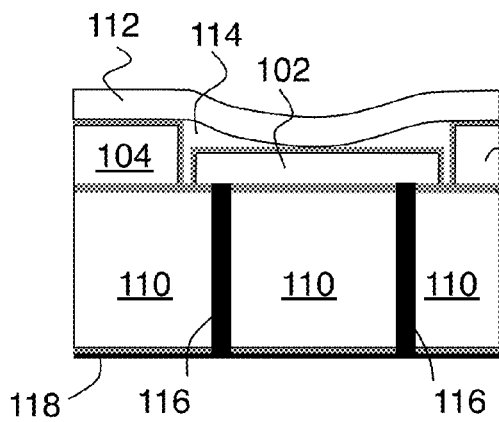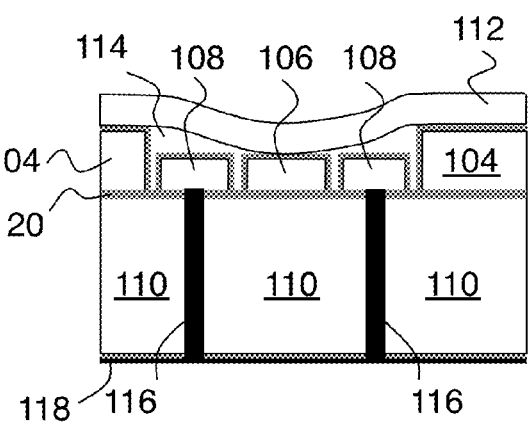
Fig. 1a   Fig. 1b
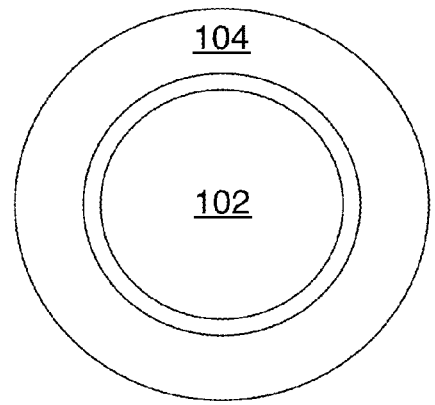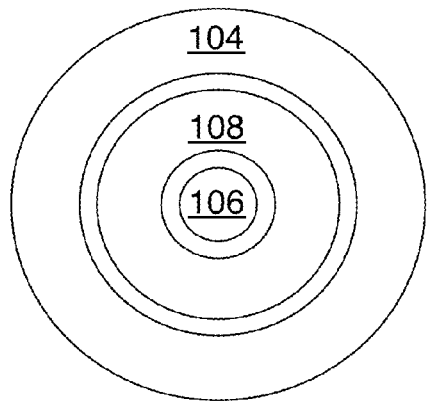
Fig. 1c   Fig. 1d

METHOD FOR OPERATING CMUTS UNDER HIGH AND VARYING PRESSURE

CROSS REFERENCE TO RELATED APPLICATIONS

This application claims the benefit of U.S. provisional patent application 61/545,788, filed on Oct. 11, 2011, entitled "Method for operating CMUTs under high and varying pressure", and hereby incorporated by reference in its entirety.

FIELD OF THE INVENTION

This invention relates to capacitive micromachined ultrasonic transducers (CMUTs).

BACKGROUND

Capacitive micromachined ultrasonic transducers (CMUTs) have been used for various applications for many years. However, there remain CMUT applications for which conventional CMUT approaches do not work well. One such application is operation in gas over a wide pressure range. The main difficulty with conventional CMUT operation over a large pressure range is that the CMUT plate will tend to be in contact with the substrate at the higher part of the pressure range, and not in contact with the substrate at lower pressures. CMUT performance depends significantly on whether or not the CMUT plate touches the substrate, so there will be significant (and undesirable) variation in device performance over the pressure range.

One conventional way to avoid this problem is to design the CMUT such that the CMUT plate does not touch the substrate at any part of the pressure range. However, this approach would undesirably lower device efficiency, especially at the low end of the pressure range.

Accordingly, it would be an advance in the art to provide improved CMUT performance over a wide pressure range.

SUMMARY

The above-identified problem is addressed in the present work by providing a CMUT in permanent contact mode. Such a CMUT always has its plate in contact with the substrate, even for zero applied electrical bias. This contact is provided by the pressure difference between the environment (typically 1 atm or greater), and the pressure of the evacuated region between the CMUT plate and substrate (typically 1 mTorr or less).

Due to this permanent contact, the electric field in the gap for a given DC bias voltage will be larger, which provides improved coupling efficiency at lower DC bias voltages. Furthermore, in an environment with high and varying pressure, the plate will not shift between the conventional mode and the collapsed mode, but will only be pushed down with varying contact radius.

In some embodiments, an electrode shaped as an annulus is employed, so that only the active vibrating part of the CMUT plate sees the applied DC and AC voltages.

The permanent contact operation mode provides significant advantages:
1) More stable frequency, static operational point, and improved coupling efficiency: Due to the permanent contact, the electric field in the gap will be larger, which provides improved coupling efficiency at lower DC bias voltages. Furthermore, in an environment with high and varying pressure, the plate will not shift between the conventional mode and the collapsed mode, but will only be pushed down with varying contact radius; this provides more stable resonant frequencies and static operation point for CMUTs. For the same reason this device should also be more stable when a mechanical push is acting on the front face of the transducer, which is beneficial for medical and therapeutic devices.
2) No collapse voltage required: The plate is in contact with the bottom of the cavity even at 1 atm pressure and without any DC bias. This eliminates the need for applying a high DC bias during operation to collapse the CMUTs, or the need for using a high DC bias to pull in the plate during fabrication to permanently fix the plate in contact.
3) In some embodiments, a wafer bonded plate process is employed for fabrication, which gives more design flexibility especially for large devices for ultrasonic flow metering (UFM) applications.

A partial electrode for permanent contact devices also provides significant advantages:
1) Less breakdown: The partial electrode removes the high electric field in the contact region, thus reducing the risk of electric breakdown and improving device reliability
2) Reduced parasitics thereby improving coupling efficiency: Since the permanently contacting part of the plate will not be moving at all, if electric field is applied to this region, it will contribute to the parasitic capacitance (instead of the active capacitance) of the transducer. The partial electrode allows only the active vibrating part of the plate to see the applied DC and AC voltages. This reduces the parasitic capacitance introduced by the permanently contacting region and thus improves the coupling efficiency.

The permanent contact operational mode for CMUTs greatly benefits any applications with large and/or varying pressure, or mechanical force, on the transducer surface. Examples include: (1) medical and therapeutic devices, where mechanical push on the transducers is possible, (2) the ultrasonic flow metering (UFM) of flare gas, which can have a significant impact on exhaust monitoring as well as the monitoring for compliance with environmental regulations, and (3) any other applications requiring the ultrasonic transducers to function under high and/or varying pressures, such as chemical sensing, range finding, and non-destructive evaluation in harsh environments.

BRIEF DESCRIPTION OF THE DRAWINGS

FIGS. 1a-d show some embodiments of the invention.

DETAILED DESCRIPTION

Figure 2:
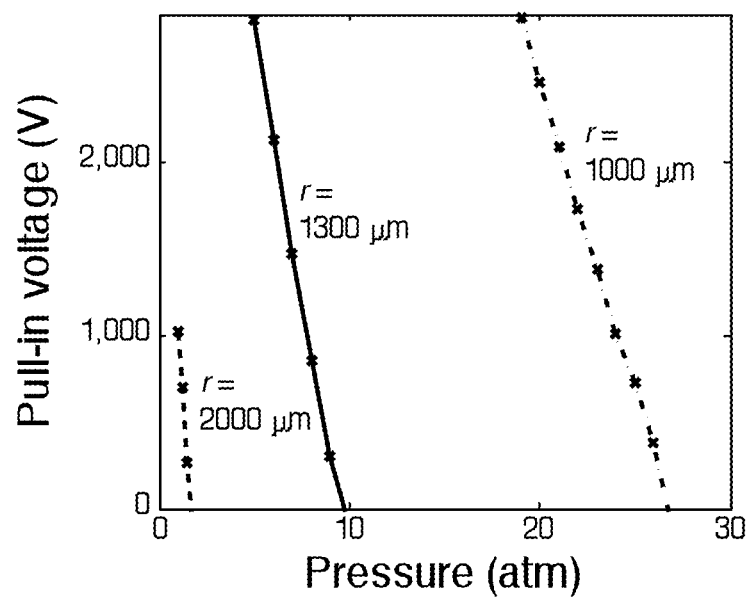
FIG. 2 shows pull-in voltage vs. pressure for conventional CMUTs of various radius.

FIGS. 1a-d show some exemplary CMUTs according to these principles. FIG. 1a is a side view of a full-electrode CMUT, and FIG. 1b is a side view of a partial-electrode CMUT. FIGS. 1c and 1d are top views corresponding to FIGS. 1a and 1b respectively. In the example of FIGS. 1a and 1c, a CMUT plate 112 is disposed above base layer 110. An electrode 102 is connected to a back side contact 118 by vias 116. The separation between plate 112 and base layer 110 is defined by a support layer 104. As described in greater detail below, an insulating layer 120 (e.g., silicon oxide) separates base layer 110 from support layer 104 and from electrode 102. On these figures, oxide features are shown with gray lines. It is convenient to define the substrate of the CMUT as including base layer 110 and electrode 102. As shown, CMUT plate 112 makes partial contact with the substrate when no external bias voltage is applied to the CMUT. A sealed cavity 114 between CMUT plate 112 and the substrate is substantially evacuated (pressure preferably less than 1 mTorr, more preferably less than about $5*10^{-3}$ µTorr). The CMUT is configured to operate at an external gas pressure of about 1 atmosphere or more (e.g., over a range from about 1 atm to about 20 atm). The difference between this external pressure and the pressure in cavity 114 is sufficient to force plate 112 into partial contact with the substrate.

The example of FIGS. 1b and 1d is similar to the example of FIGS. 1a and 1c, except that electrode 102 on FIGS. 1a and 1c is replaced with an electrode 108 shaped as an annulus that surrounds a contact zone where the CMUT plate 112 makes contact with the substrate. Here, the substrate includes base layer 110, electrode 108, and floating structure 106.

A) Finite Element Design Example

This section relates to exemplary design considerations for a flare gas metering application.

A1) Introduction

In ultrasonic transit time gas flow meters, at least one pair of transducers is used to transmit and receive ultrasound up-stream and down-stream. From the difference in transit times, one can calculate the velocity of the flow. Various UFM schemes have been explored to improve the flow meter performance in terms of rangeability.

Ultrasonic flow meters are generally designed for specific environmental conditions, such as a certain pressure range. In an exemplary target application (flare gas metering), the pressure ranges from 1 to 20 atm. In terms of flow velocity we face 80 dB dynamic range (0.01-100 m/s). Further, we aim for frequencies in the range of 300 kHz and temperatures up to 300° C. Conventional CMUT approaches have difficulty with this set of requirements, especially the pressure range.

The varying pressure range can be considered challenging for piezoelectric transducers due to acoustic impedance mismatch, especially at the lower pressure range. CMUTs are known to be efficient in gases, but the static DC operation point of a conventionally operated CMUT plate varies significantly with pressure. The plate can be brought in contact with the bottom of the evacuated cavity at low pressure, which results in a dramatic change in device behavior [e.g., (0,1)-mode frequency approximately doubles, the total device capacitance increases, as well as the coupling efficiency]. All of these can happen even without a change of the DC bias voltage, i.e. just due to the change in ambient pressure. On the other hand, if we design the gap to be large enough so that the plate never gets into contact with the bottom of the cavity even at a higher pressure, the device performance is severely degraded, in particular in the lower pressure range.

To address this challenge, we consider operating the CMUTs with the plate in permanent contact with the bottom of the cavity already at 1 atm ambient pressure and zero DC bias. With increasing pressure the contact area between the CMUT plate and the bottom of the cavity increases, which results in a more gradual change in static operational point.

A2) Finite Element Analysis (FEA)

A 2-D axial symmetric model was set up in the FEA software ANSYS®. A waveguide approach was used, so this model assumes a single cell surrounded by an infinite number of neighboring cells. A uniform surface load ranging from 1 to 20 atm was applied as parameter for all calculations. Because some of the designs simulated have a large deflection-to-thickness ratio, geometric nonlinearities (stress stiffening effect) must be included in the model.

First, we started with a static analysis at 1 atm and 0 V bias voltage to calculate the plate deflection profile for various geometries (diameters, plate thicknesses). Then the gap height for the next run was set slightly smaller than the previously calculated deflection at the center of the plate. This ensures contact between plate and the bottom of the cavity already at 1 atm and 0 V.

With the gap height determined, we used a modal analysis over ambient pressures ranging from 1-20 atm, and DC bias voltages ranging from 0-800 V to calculate the (0,1)-frequency over the entire geometry design space (cell diameters sizes, plate thicknesses). The output of this calculation are suitable designs that operate in the desired operation frequency range for our application (~300 kHz or below).

In addition, with another static analysis calculation the static and free capacitances were determined, based on the plate deflection profiles over 1-20 atm and 0-800 V. The equations used for static and free capacitances and the coupling efficiency $kT^2$ are taken from the literature, and are rewritten here in their discretized form (i refers to each transducer element in the FEA model, which corresponds to a ring in the axial symmetric model):

$$C^S(\text{static}) = C(V)|_{V_{DC}} \quad (1)$$
$$= \sum_{element\_ring\_i} \left(C_{gap_i}^{-1} + C_{ox_i}^{-1}\right)^{-1}$$
$$= \sum_i \frac{\varepsilon_0 A_i}{(d_0 - deflection_i) + t_{ox}/\varepsilon_{ox}}$$

$$C^T(\text{free}) = \frac{dQ(V)}{dV}\bigg|_{V_{DC}} \quad (2)$$
$$= \frac{d}{dV}(VC^S)\bigg|_{V_{DC}}$$
$$= C^S + V\frac{dC^S}{dV}\bigg|_{V_{DC}}$$
$$= C^S + V_{DC}\frac{C_i^S - C_{i-1}^S}{V_{bias_i} - V_{bias_{i-1}}}$$

$$k_T^2 = 1 - C^S/C^T \quad (3)$$

Finally, another static analysis was carried out to determine the pull-in voltage of CMUTs operated in the conventional mode.

A3) FEA Results

The pull-in voltage as a function of pressure is plotted in FIG. 2 for CMUT cells operated in conventional mode. The device dimensions chosen for illustration purposes are a 40-µm thick plate, a 36-µm gap height, 3.3-µm thick insulation layer, and three cell radii (1000, 1300, and 2000 µm). For all three designs the pull-in voltage changes from almost 3000 V down to zero within a few atm change in pressure. As expected, this demonstrates the large change in terms of static operational point of these CMUTs with varying pressure.

Figure 3A:
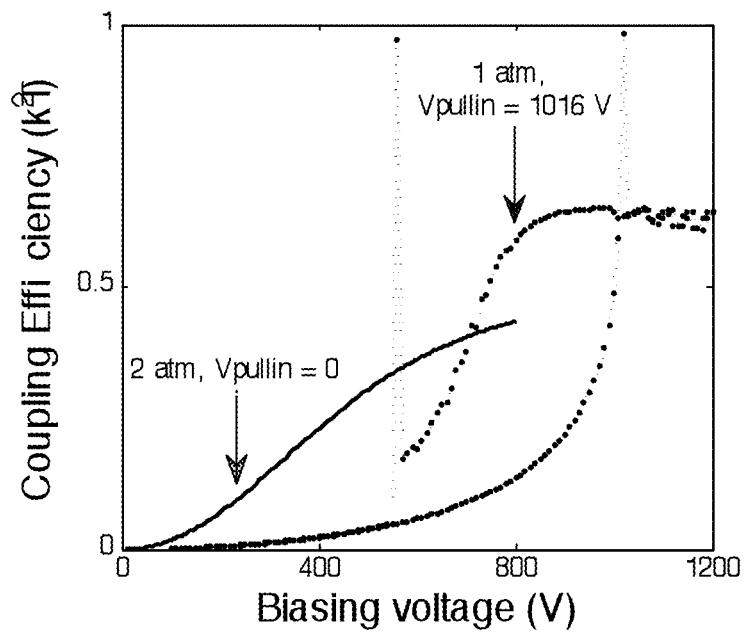
FIGS. 3a-b show coupling efficiency vs. bias voltage for CMUTs in conventional mode and in contact mode.
Figure 3B:
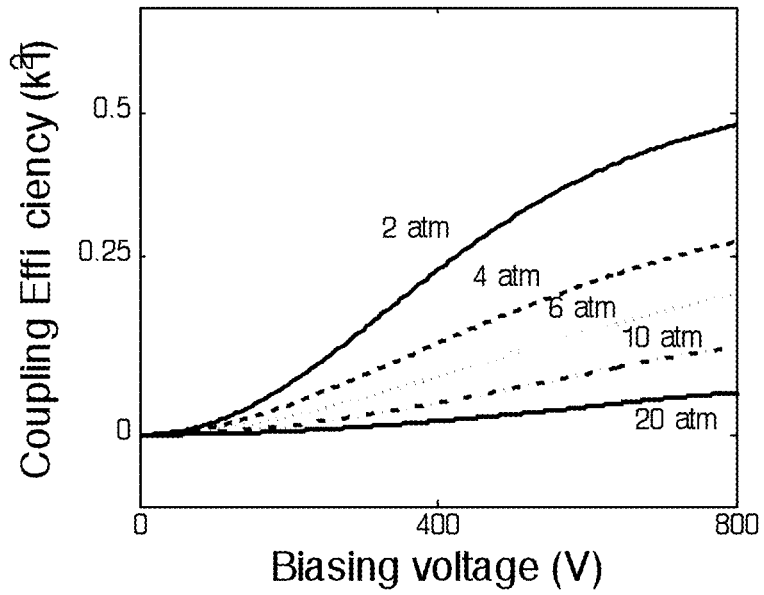

In FIGS. 3a-b we show the coupling efficiency $kT^2$ of the design with 40-μm thick plate, 36 μm gap, 3.3 μm insulation layer, and cell radius of 2000 μm. The 1-atm curve in FIG. 3a shows the coupling efficiency as a function of DC voltage for a conventional CMUT, with a pull-in voltage of 1016 V and a pull-out voltage of ~550 V. Typical for a device that experiences pull-in is hysteresis, which does not exist in permanent contact CMUTs. A higher coupling efficiency can be achieved in the collapse mode, but this requires the CMUT to be first biased at a voltage higher than the pull-in voltage and then at a voltage larger than the pull-out voltage. In most designs, biasing the device above the pull-in voltage results in a high electric field strength in the insulation layer (risk of electrical breakdown) during the time of first contact between plate and the bottom of the cavity and the time until the bias voltage is reduced to a value slightly larger than the pull-out voltage.

As the pressure increases, the plate is brought into contact with the bottom of the cavity, starting at 2 atm and higher. As shown in FIG. 3b, the coupling efficiency change from 2 to 20 atm is monotonically rising. Furthermore, if we compare the 1 atm and 2 atm curves in FIG. 3a, we can see that for the in-contact case (2 atm) the high efficiency can be achieved at a much smaller DC bias voltage.

Figure 4:
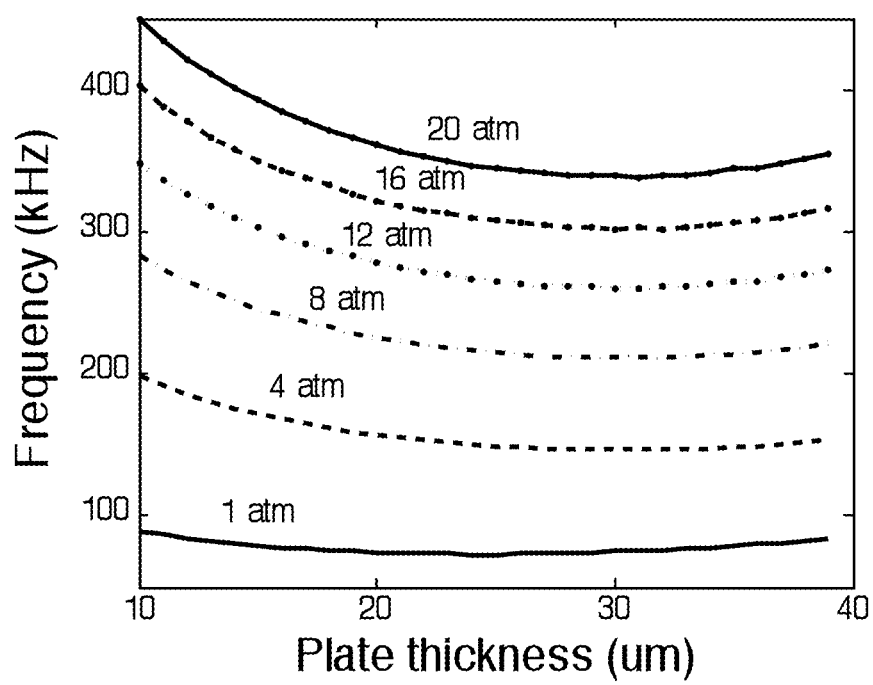
FIG. 4 shows frequency vs. plate thickness for contact mode CMUTs at various pressures.

By reducing the gap height based on our first static analysis (e.g. ~27 μm gap for a device with a 40-μm thick plate and 2000 μm radius), we achieved designs in which the plates are in permanent contact with the bottom of the cavity, even at 1 atm and zero bias. The (0,1)-mode frequency at zero DC bias of this CMUT design, obtained from the modal analysis, is presented in FIG. 4. The cell radius for all designs is 2000 μm. The gap height is chosen so that at 1 atm and zero bias the plate slightly touches the cavity bottom, which results in a different gap height for each plate thickness.

For each curve with a fixed pressure (FIG. 4), the frequency increase at low plate thickness comes from plate with a reduced vibrating portion (because a thinner plate is softer, which results in a larger contact area), while the frequency increase at high plate thickness comes from the effect of increasing stiffness on resonance frequency. Therefore, there is an optimal plate thickness that would give the smallest frequency value or range desired, which is around 27 μm for the 2000 μm cell radius design (gap height is 44 μm). This particular CMUT cell design exhibits frequencies that range from 73 to 340 kHz as the pressure goes from 1 to 20 atm.

A4) Partially Connected Electrode

The preferred choice of the CMUT fabrication process as described below (i.e., buried oxide), allows us to connect only a part of the bottom electrode to the DC bias voltage source (FIG. 1b). The objective of this idea is a reduction of the parasitic capacitance at the location of the contact area, which results in improved coupling efficiency. Further, this reduces the high electric field strength in the insulation layer at the contact area, thereby improving device reliability and reducing parasitic charging effects.

A5) Conclusion

FEA results show that permanent contact mode CMUTs have a more stable behavior over varying pressure in terms of frequency and coupling efficiency than conventional CMUTs.

B) Fabrication Example

This section provides a detailed description of an exemplary fabrication process for making embodiments of the invention.

The fabrication is based on a thick buried oxide layer in the substrate. High-temperature assisted direct wafer bonding is used. The reason why we use wafer bonding instead of sacrificial release based fabrication techniques lies in the large cell size (radii around 2000 μm) required for the targeted low frequencies (100 kHz). Thus, sacrificial release is an option for smaller cell sizes.

Figure 5A:
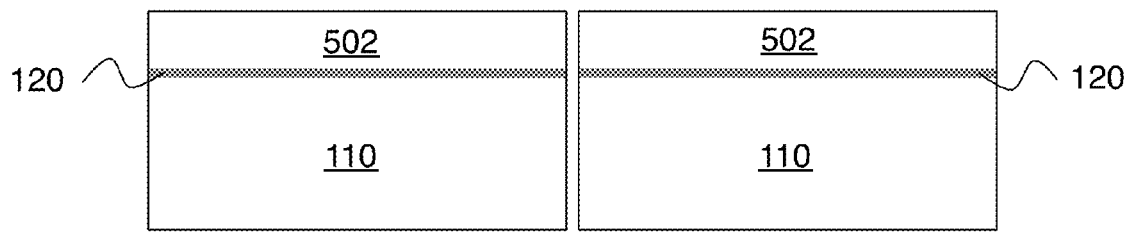
FIGS. 5a-i show an exemplary fabrication sequence according to an embodiment of the invention.
Figure 5B:
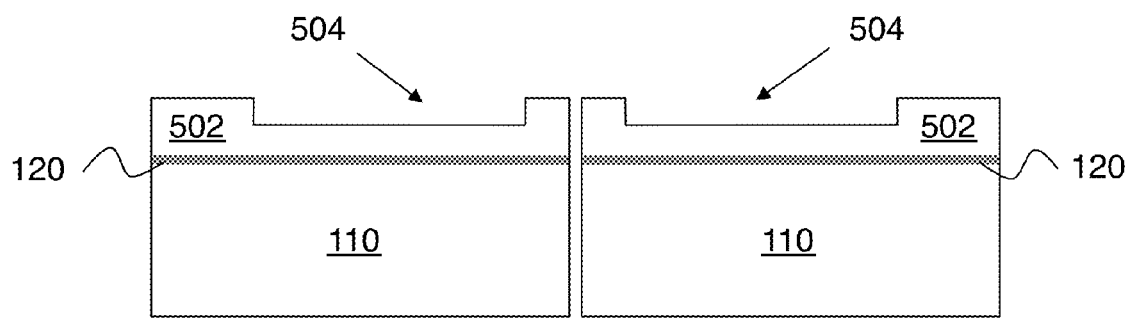

FIGS. 5a-i show an exemplary fabrication sequence. On all of these figures, a full-electrode structure is shown on the left and a partial electrode structure is shown on the right. As shown on FIG. 5a, the fabrication starts with an silicon on insulator (SOI) wafer including silicon base layer 110 and silicon cap layer 502 separated by a 3-μm-thick buried oxide layer 120. FIG. 5b shows the result of the first lithography step followed by a deep reactive ion etching (DRIE) step to define the gap height (i.e., the depth of feature 504). Due to the large gap heights (e.g., 10-30 μm), other techniques to form the gaps, such as double oxidation for accurate gap height control and good uniformity across the wafer, are not preferred.

Figure 5C:
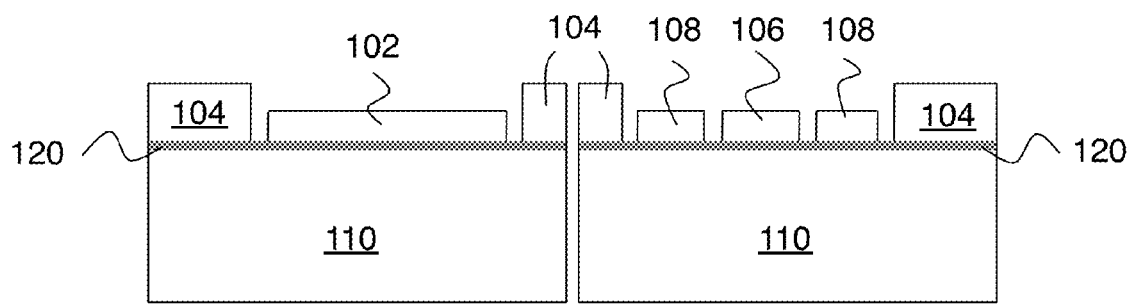
Figure 5D:
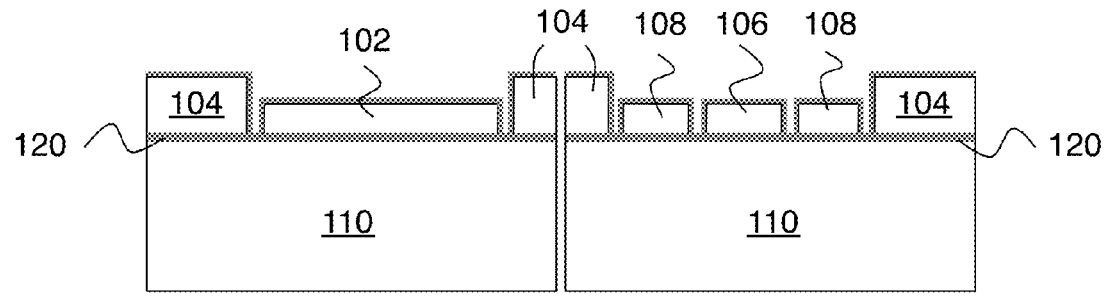

Then, a second lithography step follows to etch the vertical donut-shaped trenches down to the buried oxide layer 120 to isolate individual electrodes, as shown on FIG. 5c. For cells with partially connected electrodes, an additional donut trench with a smaller diameter is etched by DRIE to define the central non-contacted island in the bottom electrode, as shown on the right side of FIG. 5c. The wafer is then oxidized to grow a 3-μm-thick insulation layer of silicon oxide, as shown by gray lines on FIG. 5d.

Figure 5E:
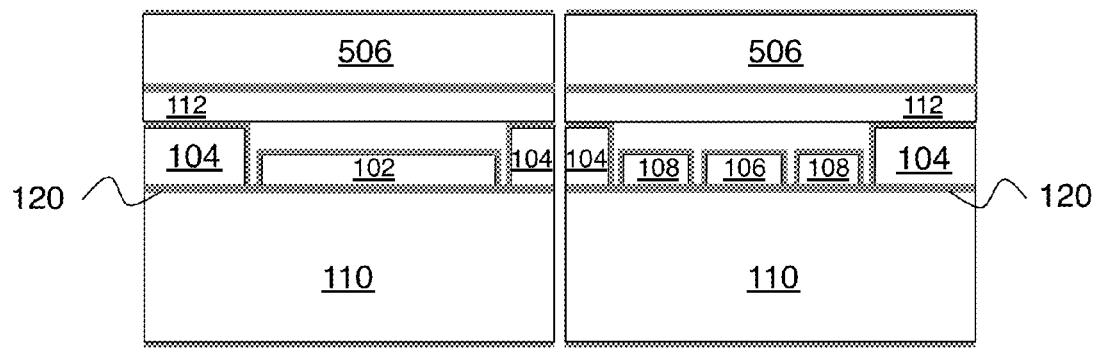
Figure 5F:
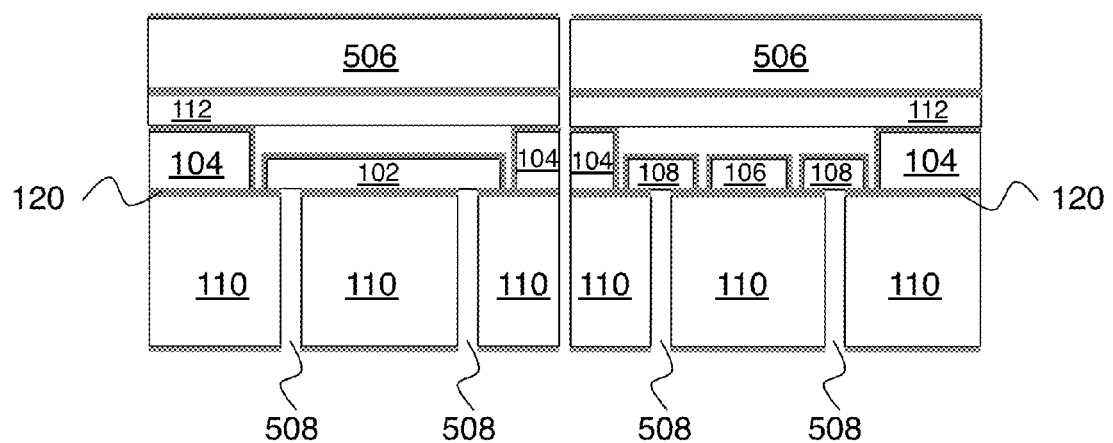
Figure 5G:
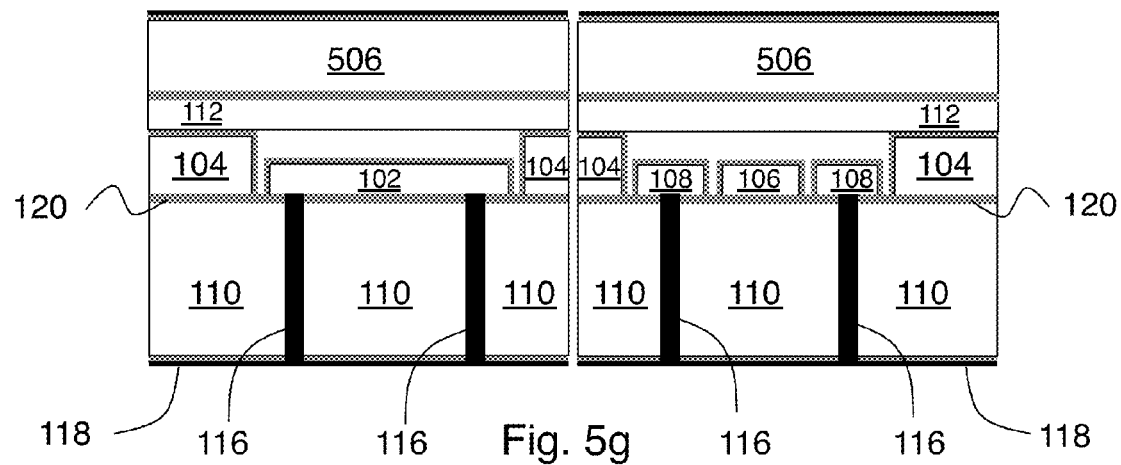
Figure 5H:
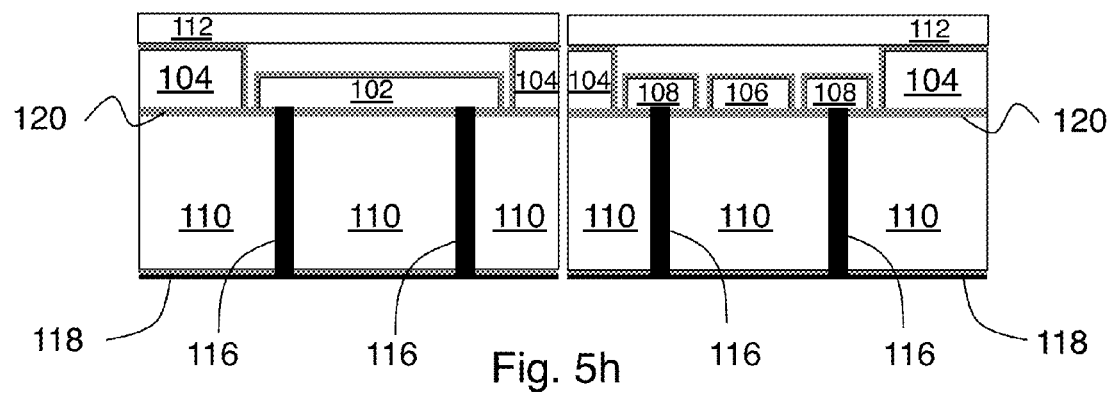
Figure 5I:
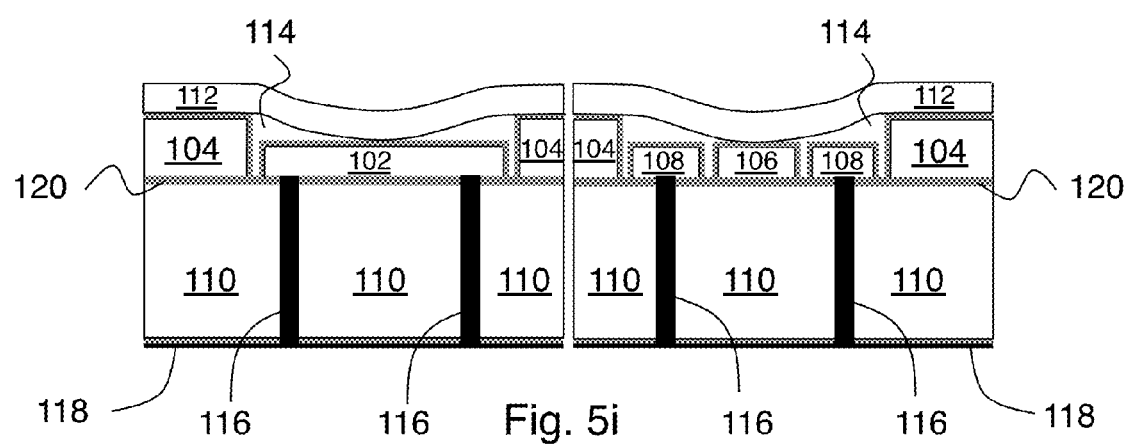

Next, the wafer is high-temperature assisted direct bonded to another SOI wafer (having handle layer 506 and plate layer 112 separated by oxide) with the plate layer thickness equal to the desired CMUT plate thickness (e.g., 30-60 μm), as shown on FIG. 5e, and annealed at 1100° C. This wafer bonding can be performed at low pressure to form the substantially evacuated cavity between the CMUT plate and the substrate.

Now with the CMUT cavities sealed and protected from contamination and with strong mechanical support, the wafer is ready for the backside vias etch step thru silicon (e.g., by DRIE). The buried oxide layer 120 acts as an etching stop, and can then be opened by plasma and HF vapor etching to provide openings 508, as shown on FIG. 5f. Immediately after the HF vapor step, a 5-μm-thick polycrystalline silicon layer is deposited (e.g., by low pressure chemical vapor deposition (LPCVD)) with intermediate doping iterations (1-μm+2-μm+2-μm) to provide electrical connection from the wafer backside to the bottom electrode of the CMUT cavity by polysilicon vias 116 and polysilicon back side contact 118, as shown on FIG. 5g.

Then the CMUT plate is released by 3 steps: (1) mechanically grinding down handle layer 506 (e.g., to about ~100 μm thickness); (2) using an isotropic etching recipe in a DRIE tool to remove the remaining silicon of handle layer 506; and (3) removing the buried oxide layer of the plate SOI wafer via buffered oxide etch (BOE) solution, with results as shown on FIG. 5h. Finally, a metallization and litho step is used, and the plate is etched to define individual devices before the wafer is diced (Not shown in FIGS. 5a-i).

To make sure that we obtain devices that have plates in permanent contact with the bottom electrode, we intentionally varied the cell radii, ranging from 1800 to 2200 um, the gap heights, and plate thicknesses for our first fabrication run. Notice that the permanent contact already happens during the plate releasing step (FIG. 5h) after the majority of the silicon in the handle layer is removed, resulting in the cross sectional view as in FIG. 5i.

There are fabrication processes suitable for producing permanent contact CMUTs other than the process of the above example. The idea of operating CMUTs in the permanent contact mode can be applied in any of the CMUT fabrication processes, as long as the gap height is chosen carefully according to the plate thickness and cell radius, so that the plate slightly touches the bottom of the cavity at 1 atm and zero DC bias.

The partial electrode structure can be realized in several ways. One alternative is to form a thick oxide region in the center of a single electrode, which has the same effect as the central floating silicon in FIG. 1b, providing a smaller parasitic capacitance and smaller electric field for the contacting region.

Variations of this fabrication sequence are applicable. For example, the preceding example shows defining the CMUT gap height by patterning the base SOI wafer. The CMUT gap height can also be defined by patterning the plate SOI wafer, although the wafer bonding would then need to be aligned. Another approach for defining the CMUT gap height is to bond a silicon wafer to the base SOI wafer, pattern the silicon wafer, and then bond the plate SOI on top. Double fusion bonding is required for this variation. A further variation is to etch the features that define the electrode prior to defining the CMUT gap height.

C) Experimental Results

This section describes some experimental results relating to embodiments of the invention.

C1) Measurements at Elevated Pressure

A pressurized chamber and fixtures for the devices were built to perform measurements at elevated pressure.

Each fixture contains a printed circuit board (PCB) with the required circuitry (e.g. pre-amplifier for the receiving device) and also allows for a small tilt and translation adjustments so that we can align the devices during pitch-catch measurements. The fixtures are inserted into the pressure chamber, each through a NPT (National Pipe Thread) plug with some polytetrafluoroethylene-based sealing paste applied to prevent air leakage. Through the NPT plugs, the electrical connections to the outside are established, so that bias-Ts and cables can be connected. An air compressor pumps air into the chamber and supplies the required pressure.

At each pressure, the electrical impedances for both devices in the chamber are measured at various DC bias voltages. Open and short circuit resonances are then extracted from the impedance data as a function of the DC bias. This information is used to determine the optimal DC bias combination for the two CMUTs and the frequency for the excitation signal (sinusoidal burst) for pitch-catch measurements.

C2) Electrical Impedance Measurements

The electrical impedance is measured by an impedance analyzer HP 4192A (now Agilent Technologies Inc., Palo Alto, Calif., USA). The raw impedance data is adjusted by the measured data of the standard calibration kit (open & short loads). As an example, the measured input impedance of a CMUT operated at a DC bias voltage of 250 V at various pressures ranging from 1 to 8 atm is presented in FIG. 6a. The single-cell CMUT has a cell radius of 2100 µm, a 75% partial electrode (active radius=0.75 total radius), a 60-µm thick single crystal silicon plate, and a 8-µm gap height.

Figure 6A:
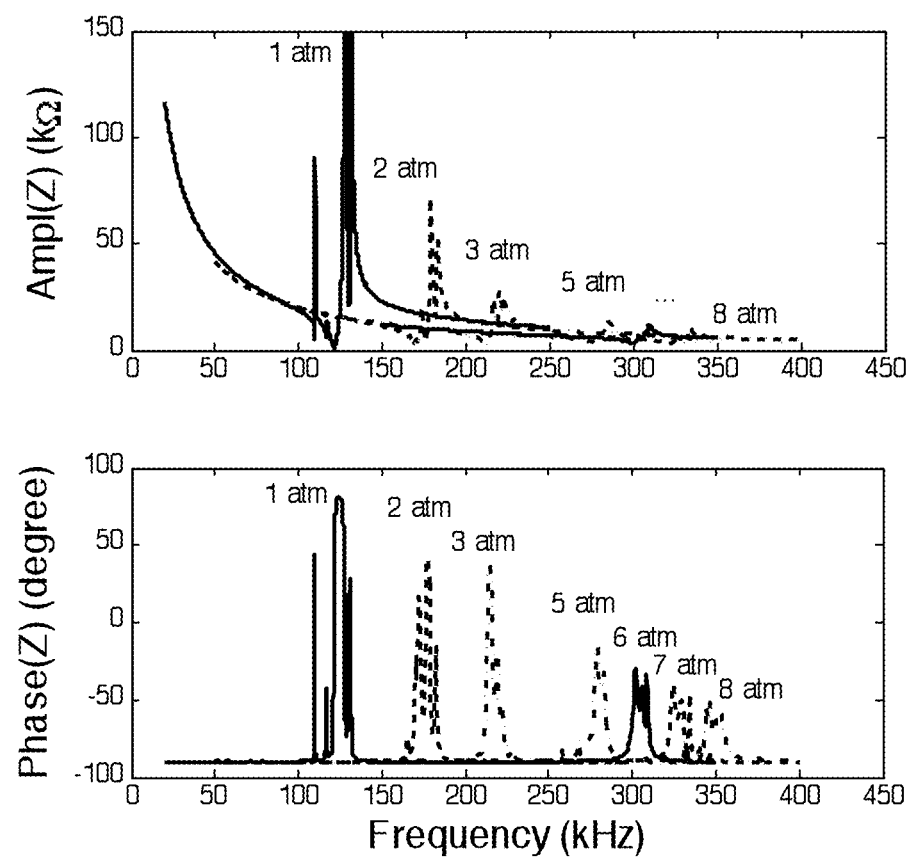
FIGS. 6a-b show a comparison between measured impedance and modeled impedance for permanent-contact-mode CMUTs at various pressures.
Figure 6B:
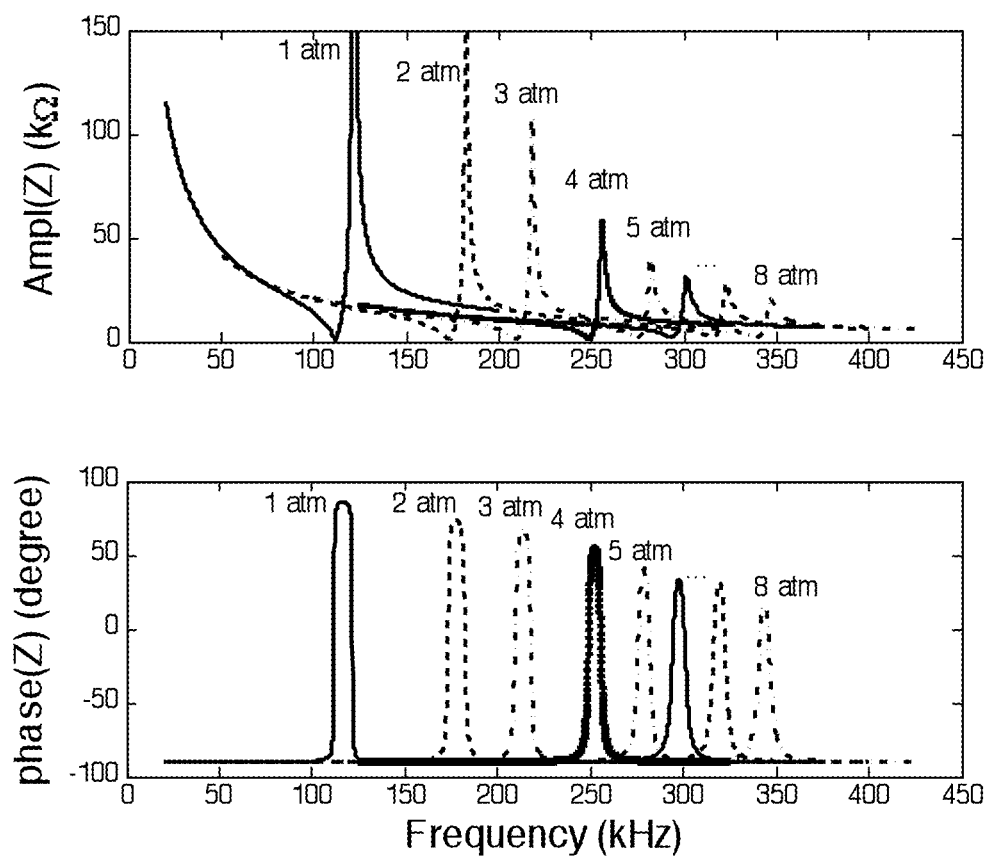

An FEA was performed for this CMUT design, with results as in FIG. 6b. The simulation uses the linear harmonic analysis in ANSYS with medium loading on top of a single CMUT cell and with an added parallel parasitic capacitance of 29 pF. The medium properties, such as air density as a function of pressure, are included in the model accordingly.

The direct comparison reveals a good agreement between our measurements and FEA results. In both cases, when the pressure increases, the resonant frequencies increase, and the magnitude of the impedance decreases (FIGS. 6a-b). This is because the plate is pushed more against the bottom of the cavity at higher pressures, and thus the actual vibrating portion of the plate decreases. The FEA overestimates the magnitude of the electrical impedance because it does not contain all loss mechanisms that are present in the CMUT device.

Figure 7:
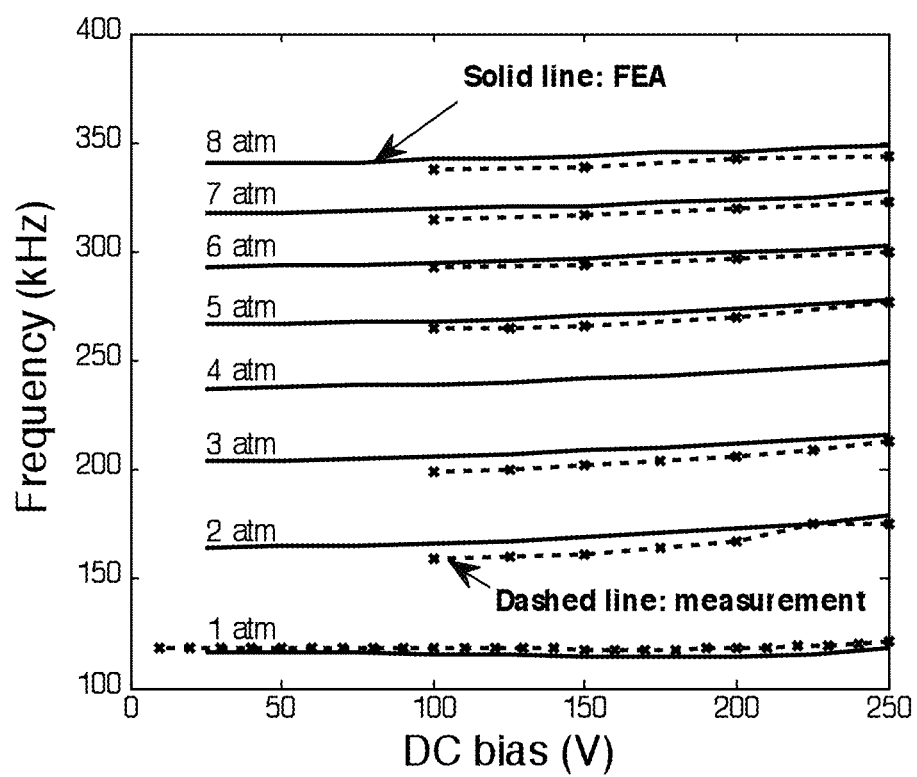
FIG. 7 shows measured and modeled frequency vs. bias for CMUTs in permanent contact at various pressures.

The open-circuit and short-circuit resonances can be extracted from the impedance data of FIGS. 6a-b. The short-circuit resonances extracted from measurements are compared to the nonlinear modal analysis results from ANSYS in FIG. 7, and again the simulation agrees with the measurement. Furthermore, the frequencies obtained from the nonlinear modal analysis agrees with those from the linear harmonic results, which implies that for our devices in the permanent contact mode, the model does not demonstrate obvious stress stiffening effects and thus the linear harmonic analysis is valid.

C3) Pitch-Catch Measurements

In the pitch-catch measurement setup, the transmitting device is driven by a function generator (HP33120A, now Agilent Technologies Inc., Palo Alto, Calif., USA) which has a low output impedance of 50Ω, and the receiving device is connected to a pre-amplifier which has high input impedance in the MΩ range. Since matching the impedance will give maximum power transmission, the transmitting CMUT will perform the best at the short-circuit resonance where the device impedance is at a minimum, and the receiving CMUT will perform the best at the open-circuit resonance where the device impedance is at a maximum. Hence, the implication is that, even for two identical CMUTs, simply applying identical values for the DC bias voltage on the two devices will not make them transmit and receive at the same frequency efficiently. Note that the underlying assumption is that the bandwidth of the CMUT is narrow enough, which is the case for our single cell devices used for this work. For optimum pitch-catch performance, we purposely tune the DC bias voltages applied to the transmitting and receiving CMUTs separately, and thus, the operating frequencies are matched during the pitch-catch measurements for maximum response.

Figure 8A:
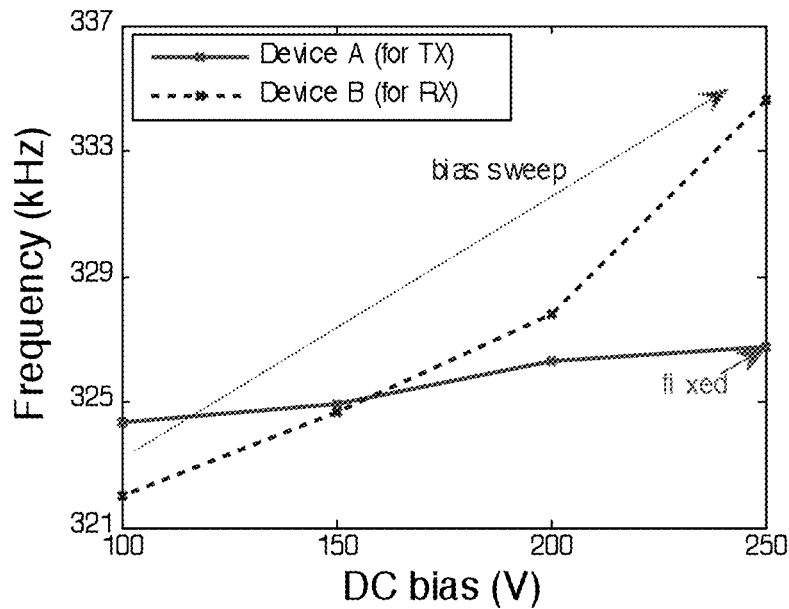
FIGS. 8a-c shows results of a pitch-catch experiment with permanent contact CMUTs.
Figure 8B:
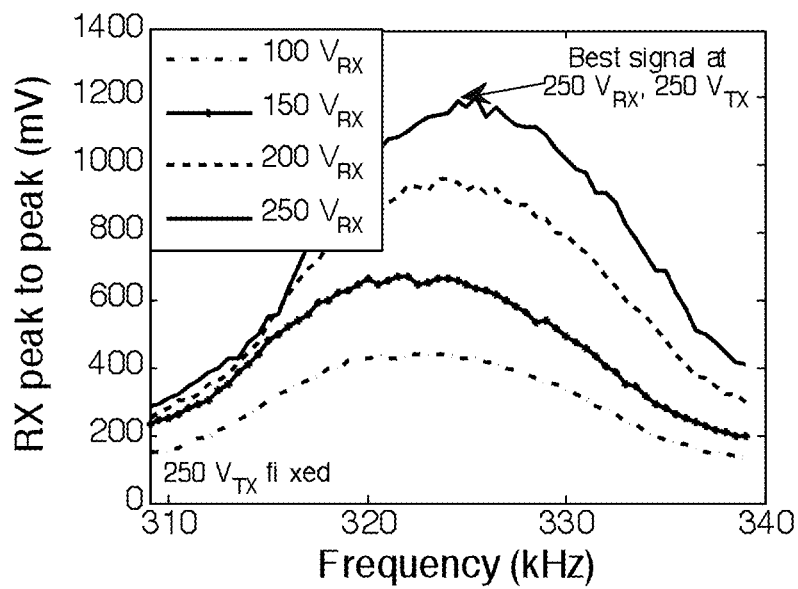
Figure 8C:
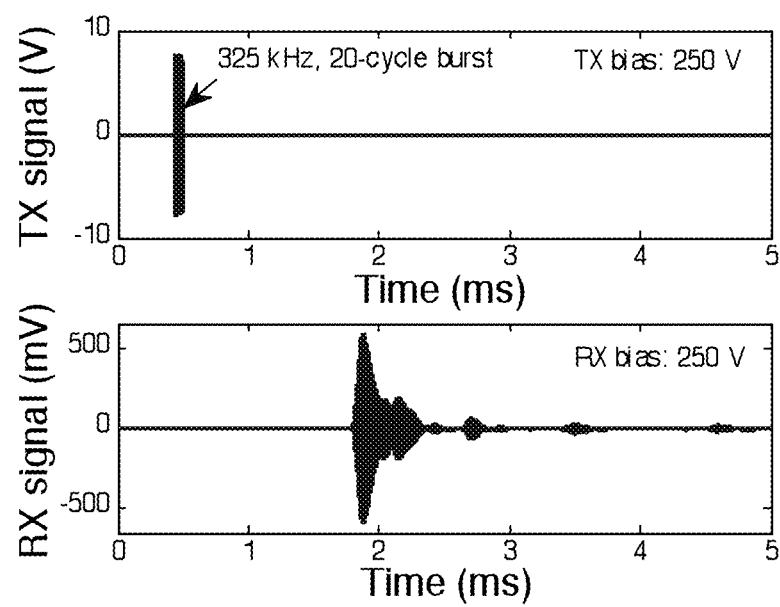

The pitch-catch measurement results at 7 atm are given in FIGS. 8a-c. Device B is the same CMUT that has been described the previous section for electrical impedance measurements, while Device A has a radius of 2000 µm, a 50% electrode (active radius=0.5 total radius), a 60-µm thick plate, and a 8-µm gap height.

FIG. 8a shows the short circuit resonance for the transmitting Device A and the open circuit resonance for the receiving Device B at 7 atm, which are extracted from the electrical impedance measurement, as a function of DC bias voltages. With VTX fixed at 250 V and VRX sweeping from 100 to 250 V, the frequency matching point should occur at VRX~185 V, which is too low to provide good operating efficiency. Therefore, the best signal occurs when both VTX and VRX are at 250 V.

In short, the optimal biasing scheme involves both tuning the individual DC biases to achieve matching frequency, as well as choosing higher DC bias for better coupling efficiency. Sometimes we can achieve both criterions, but other times when a matched frequency can only be attained by low DC bias voltages, the effect that higher biasing voltages give higher coupling efficiency will take over.

To validate our frequency matching method to determine the optimal biasing scheme for the pitch-catch devices, a series of pitch-catch measurements are performed as VTX is fixed at 250 V, and VRX sweeps from 175 to 250 V. For each DC bias combination, a 20-cycle sinusoidal burst signal with frequency sweeping over the range of interest is applied to the transmitting device. As indicated in FIG. 8b, the best signal occurs at VTX=250 V, and VRX=250 V, which is not where the frequencies match. Considering the transit time difference over different paths inside the chamber, only the first 0.24 ms of the receiving signal is considered in extracting the RX peak-to-peak value in FIG. 8b.

FIG. 8c shows time-domain signals corresponding to the best case of FIG. 8b. As can be seen in FIG. 8c, interference is present in the received signal. Note that even at 7 atm, we are able to obtain a received signal with good signal-to-noise ratio of 45 dB.

C4) Conclusion

We successfully demonstrated that our CMUTs can handle elevated pressures up to 8 atm. Electrical impedance measured shows good agreement with the results of both the linear harmonic and the nonlinear modal analysis of ANSYS. Pitch-catch measurements validate our frequency matching method to determine the optimal biasing scheme for the device pair, and a received signal with good signal-to-noise ratio can be measured even at 7 atm.

The invention claimed is:

1. A capacitive micromachined ultrasonic transducer (CMUT) comprising:
   a substrate;
   a CMUT plate disposed above the substrate, wherein a sealed cavity between the substrate and the CMUT plate is substantially evacuated;
   wherein the CMUT is configured to operate at an external gas pressure of about 1 atmosphere or more;
   wherein the CMUT plate makes partial contact with the substrate when no external bias voltage is applied to the CMUT due to the external gas pressure;
   wherein a contact between the CMUT plate and the substrate is configured to have a contact radius that varies with applied pressure;
   wherein the CMUT is configured such that an active part of the CMUT plate vibrates at an operating frequency of the CMUT during operation of the CMUT;
   wherein at least one electrode of the CMUT is configured as an annulus surrounding a contact zone where the CMUT plate makes contact with the substrate;
   wherein the annulus surrounds an electrically floating region of the CMUT, whereby an electric field in the contact zone is decreased.

2. The CMUT of claim 1, wherein the external gas pressure can vary in a range from about 1 atmosphere to about 20 atmospheres.

3. The CMUT of claim 1, wherein the operating frequency of the CMUT is about 300 kHz or less.

* * * * *